United States Patent [19]

Miller

[11] Patent Number: 4,820,815
[45] Date of Patent: Apr. 11, 1989

[54] AZETIDINONE N-PHOSPHONOMETHYL ESTERS

[75] Inventor: Marvin J. Miller, South Bend, Ind.

[73] Assignee: University of Notre Dame du Lac, Notre Dame, Ind.

[21] Appl. No.: 91,804

[22] Filed: Sep. 1, 1987

[51] Int. Cl.$^4$ .............................................. C07F 9/65
[52] U.S. Cl. .................... 540/200; 540/363; 540/364; 540/205; 548/112; 548/406; 548/413; 560/170; 560/169; 562/564; 562/567
[58] Field of Search ................ 540/200, 363, 364

[56] References Cited

PUBLICATIONS

Derwent Abstract of Kyowa Hakko Kogyo, Japan Application No. J5 7091-991.
Herdewijn, Chem. Abs. 101, 38237z (1983).
Hirata, Chem. Abs. 93, 150115a (1978).

*Primary Examiner*—Mark L. Berch
*Attorney, Agent, or Firm*—William B. Scanlon; Leroy Whitaker

[57] ABSTRACT

The invention provides azetidinones of the formula

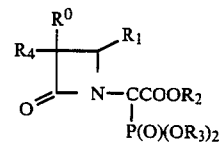

where $R_4$ is hydrogen, amino or protected amino; $R^0$ is H when $R_4$ is amino or protected amino, or $C_1$–$C_4$ alkyl when $R_4$ is H; $R_1$ is H, $CH_3$, $-(CH_2)_n Y$ where Y is OH, protected OH, $-CH_2OH$, protected $-CH_2OH$, halogen, COOH or protected COOH; n is 1 or 2; $-(CH_2)-C(O)SR_1'$ where $R_1'$ is e.g., $C_1$–$C_4$ alkyl; $R_2$ is H or protecting group and $R_3$ is e.g., alkyl or phenyl. The azetidinones obtained are useful intermediates to carbapenems and carbacephems and monocyclic antibacterials, e.g., α-(dialkylphosphono)-[[3β-[2-(2-aminothiazol-4-yl)-2-(syn)methoxyiminoacetylamino]azetidin-2-one-1-yl]]acetic acid and pharmaceutically acceptable salts thereof.

17 Claims, No Drawings

AZETIDINONE N-PHOSPHONOMETHYL ESTERS

BACKGROUND OF THE INVENTION

This invention relates to β-lactam antibiotics. In particular, it relates to a process and intermediates for preparing azetidin-2-ones substituted on the ring nitrogen with an α-(dialkyl or diarylphosphono)carboxymethyl group which are useful as antibacterials and as intermediates to bicyclic antibiotics.

Since the discovery of the monocyclic β-lactam antibiotics and the carbapenems and carbacephems, considerable effort has been undertaken to provide synthetic routes for preparing these antibacterials. Often, the elaboration of the 4-membered β-lactam ring is the key to the preparative route. U.S. Pat. No. 4,595,532 describes a process for preparing N-[(diethoxycarbonyl)methyl]substituted azetidinones and related esters via cyclization of β-hydroxy amides formed with diethyl aminomalonate and β-hydroxy acids. The process of this invention provides N-[(α-phosphono)carboxymethyl]azetidinones via cyclization of β-hydroxy amides formed with aminophosphonoacetates and β-hydroxy acids.

SUMMARY

3β-Protected amino- or 3α-alkyl-4-substituted azetidin-2-ones substituted on the ring nitrogen by an α-phosphonoacetate group are provided in a process comprising the triphenylphosphine-dialkyl azodicarboxylate mediated cyclization of β-hydroxy acid phosphonomethyl amides.

The azetidin-2-ones are intermediates useful for preparing bicyclic β-lactams, e.g., carbapenems and carbacephems.

DETAILED DESCRIPTION

The process of this invention provides 1-(phosphonomethyl)azetidinones represented by formula 1:

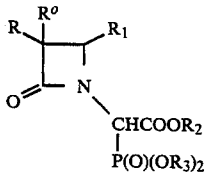

wherein R is hydrogen or protected amino;
$R^0$ is hydrogen when R is protected amino, or $C_1$-$C_4$ alkyl when R is hydrogen;
$R_1$ is hydrogen, methyl, a group represented by the formula

wherein Y is hydroxy, protected hydroxy, hydroxymethyl, protected hydroxymethyl, halogen, formyl, carboxy or protected carboxy, and n is 1 or 2; or
$R_1$ is a thio ester group represented by the formula

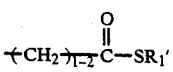

wherein $R_1'$ is $C_1$-$C_4$ alkyl, or $C_1$-$C_4$ alkyl monosubstituted by amino, acetylamino, $C_1$-$C_4$ alkylamino or di($C_1$-$C_4$alkyl)amino;
$R_2$ is hydrogen or a carboxy-protecting group; and
$R_3$ is $C_1$-$C_4$ alkyl, phenyl or benzyl and phenyl or benzyl mono-substituted by $C_1$-$C_4$ alkyl, halogen or $C_1$-$C_4$ alkoxy.

According to the process provided herein, a β-hydroxy phosphonomethyl amide represented by formula 2

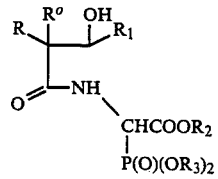

wherein R, $R^0$, $R_1$, $R_2$ and $R_3$ have the above-defined meanings, except that when Y is hydroxy, hydroxymethyl or carboxy, these groups are protected; is reacted in an inert solvent under substantially anhydrous conditions with triphenylphosphine and a di-($C_1$-$C_3$ alkyl)azodicarboxylate in an amount equimolar with the triphenylphosphine to form the azetidinone-2 represented by formula 1.

The process is carried out at a temperature of between about 0° C. and about 45° C., preferably at between about 20° C. to about 30° C. Inert solvents which can be used in the process are the common aprotic solvents such as the ethers, e.g., diethyl ether, tetrahydrofuran, dioxane and 1,2-dimethoxyethane; nitriles such as acetonitrile and halogenated hydrocarbons such as methylene chloride, ethylene dichloride or trichloroethane. A preferred solvent is tetrahydrofuran.

Di-($C_1$≈$C_3$ alkyl)azodicarboxylates used in the process are dimethyl azodicarboxylate (DMAD), diethyl azodicarboxylate (DEAD), dipropyl azodicarboxylate (DPAD) and diisopropyl azodicarboxylate (DIAD). DIAD is a preferred reagent.

The cyclization reagent, triphenylphosphinedialkyl azodicarboxylate, can be employed in a molar ratio of reagent to β-hydroxy phosphonomethyl amide (2) of between about 0.5:1 to about 10:1. Preferably, the molar ratio is about 1.5:1 to about 2.5:1. Best yields of β-lactam product have been obtained with a mole ratio of about 2.5:1.

As was noted above, free hydroxy (other than the β-hydroxy group) and carboxy groups present in 2 are desirably protected with conventional protecting groups during the process. Unprotected hydroxy and carboxy groups tend to interfere with the desired cyclization and form side products. Such protecting groups employed in the process are defined hereinafter. The benzyl or p-methoxybenzyl groups can be used to protect the hydroxy and carboxy functions, e.g., when $R_2$ is hydrogen and when Y is —OH or —COOH. Another valuable carboxy-protecting group for use in the process is the 2-trialkylsilylethyl group such as, for example, 2-(trimethylsilyl)ethyl, 2-(t-butyldimethylsilyl)ethyl and 2-[(2,3-dimethylbutan-2-yl)dimethylsilyloxy]ethyl.

The process is carried out by adding TPP to a solution of 2 in an inert solvent followed by addition of the dialkyl azodicarboxylate. The latter can be added as a solution in an inert solvent, preferably the inert solvent employed for 2. Alternatively, the TPP and dialkyl azodicarboxylate can be premixed in an inert solvent and the solution added to the solution of 2. The TPP and azodicarboxylate can form a complex which can also serve as the cyclization reagent.

The progress of the process can be monitored by thin layer chromatography with additional quantities of the reagents added to induce further β-lactam ring formation when needed.

The product 1 is recovered from the reaction mixture by conventional recovery methods. For example, the solvent is removed by evaporation and the crude product purified by chromatography over silica gel.

The terms of the above formulas 1 and 2 have the following meanings. "Protected amino" refers to a substituted amino group substituted by a conventional group commonly used with the β-lactam antibiotics for the temporary blocking of the amino group. Examples of such protected amino groups represented by R include the alkoxycarbonylamino, substituted alkoxycarbonylamino, cycloalkyloxycarbonylamino, alkenyloxycarbonylamino, alkynyloxycarbonylamino, aralkyloxycarbonylamino and bicycloalkyloxycarbonylamino groups such as the $C_1$—$C_5$ alkoxycarbonylamino group, e.g., ethoxycarbonylamino, amyloxycarbonylamino or t-butyloxycarbonylamino; 2,2,2-trichloroethoxycarbonylamino; the $C_3$-$C_6$ cycloalkoxycarbonylamino groups, e.g., cyclopropyloxycarbonylamino, cyclopentyloxycarbonylamino or cyclohexyloxycarbonylamino; the $C_3$-$C_6$ alkenyloxycarbonylamino groups, e.g., allyloxycarbonylamino or pent-2-enyloxycarbonylamino; the alkynyloxycarbonylamino groups, e.g., dimethylethynyloxycarbonylamino or diethylethynyloxycarbonylamino; the aralkyloxycarbonylamino groups, e.g., benzyloxycarbonylamino, p-nitrobenzyloxycarbonylamino or diphenylmethoxycarbonylamino; and the bicycloxycarbonylamino, e.g., adamantyloxycarbonylamino or bicycloheptyloxycarbonylamino. Protected amino also refers to phthalimido or the 4,5-diphenyl-4-oxazolin-2-one-3-yl group ("Ox" group) and to trialkylsilylamino groups such as, e.g., trimethylsilylamino, di(trimethylsilyl)amino and the cyclic disilylated amino group represented by the formula

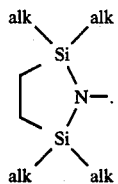

The term "$C_1$-$C_4$ alkyl" ($R^0$) refers to methyl, ethyl, n-propyl, isopropyl, n-butyl, iso-butyl and sec-butyl radicals.

The term "carboxy-protecting group" refers to a conventional carboxy-blocking group commonly used in the β-lactam antibiotic art and serves the function of blocking the acidic carboxy group while reactions are carried out at other sites in the molecule. Such groups are used for the temporary protection or blocking of the carboxy group. Examples of such groups are t-butyl, haloalkyl groups, e.g., 2,2,2-trichloroethyl, 2-iodoethyl, allyl, 1,1-dimethylprop-2-yne-1-yl, benzyl, substituted benzyl, e.g., 4-nitrobenzyl and 4-methoxybenzyl, diphenylmethyl, trialkylsilyl or mixed alkylarylsilyl groups, e.g., trimethylsilyl, triethylsilyl, dimethylphenylsilyl, β-trimethylsilylethyl, β-(t-butyldimethylsilyl)ethyl and β-methylsulfonylethyl.

When $R_1$ represents a radical $-(CH_2)_n Y$, $R_1$ can be 2-hydroxyethyl, 3-hydroxypropyl, 2-hydroxypropyl, 2-formylethyl, 3-formylpropyl, 2-carboxyethyl, 3-carboxypropyl, 2-chloroethyl, 2-bromoethyl, 3-bromopropyl, 2-iodoethyl and like groups. As was noted hereinabove, when Y is hydroxy or carboxy, the process is preferably carried out with these groups protected. Suitable hydroxy-protecting groups include benzyl, diphenylmethyl, dihydropyranyl, 2-(trimethylsilyl)ethyl, 2-(t-butyldimethylsilyl)ethyl, trimethylsilyl or other conventional hydroxy-protecting group. Suitable carboxy-protecting groups can be one of the protecting groups described hereinabove.

The thio ester group $-(CH_2)_{1-2}C(O)SR_1'$ represented by $R_1$ is exemplified by methyl thioacetate, ethyl thiopropionate, t-butyl thioacetate, 2-aminoethyl thioacetate, 2-aminoethyl thiopropionate, 2-diethylaminoethyl thioacetate, 3-dimethylaminopropyl thioacetate, 2-acetylaminoethyl thiopropionate, 2-n-propylaminopropyl thioacetate, 2-acetylaminoethyl thioacetate, 2-(N-acetyl-N-methylamino)ethyl thioacetate, 4-aminobutyl thioacetate and like thio esters.

Examples of the α-phosphonoacetate group

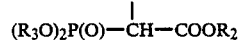

of formulas 1 and 2 are methyl α-(dimethylphosphono)acetate ($R_3=R_2=$methyl), benzyl α-(diethylphosphono)acetate ($R_3=$ethyl, $R_2=$benzyl), p-methoxybenzyl α-(diphenylphosphono)acetate ($R_3=$phenyl, $R_2=$p-methoxybenzyl), 2-(t-butyldimethylsilyl)ethyl, α-(diethylphosphono)acetate ($R_3=$ethyl, $R_2=$t-$C_4H_9(CH_3)_2Si—CH_2CH_2—$), t-butyl α-(dibenzylphosphono)acetate ($R_3=C_6H_5CH_2—$, $R_2=$t-$C_4H_9$), p-nitrobenzyl α-(dimethylphosphono)acetate ($R_3=CH_3$, $R_2=$p-nitrobenzyl) and like qroups.

The β-hydroxy phosphono amides 2 are prepared by known methods. Compounds of formula 2 wherein R is a protected amino group are obtained by coupling the α-protected amino-β-hydroxy acid with the aminophosphono acetate is represented by formula 3

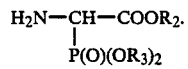

The amide-forming coupling reaction can be carried out by forming an active ester of the acid and coupling the active ester with the amino phosphono acetate. For example, the β-hydroxy acid is mixed with the aminophosphono acetate, hydroxybenzotriazole (HBT) and dicyclohexylcarbodiimide (DCC) to form the active HBT ester which then acylates the amine to provide 2. Other diimide dehydrating agents and active ester moieties can be used for the coupling. For example, 1-cyclohexyl-3-(morpholinoethyl)carbodiimide-metho-p-toluenesulfonate may be used with HBT. The N-hydroxysuccinimido esters or the N-hydroxyphthalimide esters may be used to couple the amine and acid.

Compounds 2 wherein R is hydrogen and $R^0$ is $C_1$-$C_4$ alkyl are prepared by reacting the aminophosphono acetate (3) with the chiral β-hydroxy-N-acylthiazolidin-2-thione represented by the formula in the scheme below:

phonomethyl amides are shown below wherein the captioned terms have reference to formula 2 above.

| R | $R_1$ | $R_2$ | $R_3$ |
|---|---|---|---|
| Formula 2, R = Protected Amino ||||
| t-BOCNH— | —$CH_3$ | —$C_2H_5$ | —$CH_3$ |
| CbzNH— | H | —$CH_2C_6H_5$ | —$C_2H_5$ |
| Phthalimido | —$CH_2OH$ | —$CH_2C_6H_5$ | —$CH_2C_6H_5$ |
| Ox— | —$CH_2CH_2OH$ | t-$C_4H_9$ | —$CH_2C_6H_5$ |
| Ox— | —$CH_2CH_2CHO$ | t-$C_4H_9$ | —$CH_2C_6H_5$ |
| Ox— | —$CH_2CHO$ | t-$C_4H_9$ | —$CH_2C_6H_5$ |
| Ox— | —$CH_2CH_2COOH$ | pMB | $C_6H_5$ |
| Ox— | —$CH_2C(O)SCH_3$ | pMB | $C_6H_5$ |
| Phthalimido | —$CH_2CH_2C(O)SCH_2CH_2NH_2$ | pMB | $C_6H_5$ |
| Phthalimido | —$CH_2CH_2COOH$ | —$CH_2CH_2$—$Si(CH_3)_2C_4H_9$—t | $C_2H_5$ |
| Formula 2, R = H ||||
| Ox— | —$CH_2C(O)SCH_2C_6H_5$ | t-butyl | $C_6H_5$ |
| Ox— | —$CH_2CH_2C(O)SC_2H_5$ | —$CH_2C_6H_5$ | $C_2H_5$ |
| Phthalimido | —$CH_2CH_2C(O)S$—$CH_2CH_2$—$NHCOCH_3$ | —$CH_2C_6H_5$ | $C_2H_5$ |
| Phthalimido | —$CH_2CH_2OCH_2C_6H_5$ | —$CH_2CH_2Si(CH_3)_3$ | p-chlorobenzyl |
| Ox— | —$CH_2CH_2CHO$ | —$(CH_2)_2Si(CH_3)_2$—t-$C_4H_9$ | p-chlorophenyl |

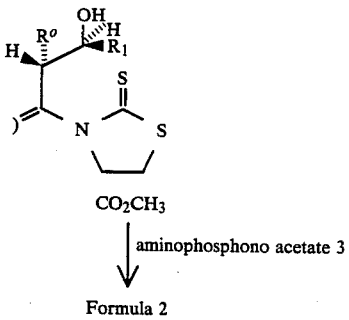

Formula 2

The reaction is best carried out in acetonitrile in the presence of a catalytic amount of 4-(dimethylamino)-pyridine (DMAP) at or near room temperature. For example, the N-acylthiazolidin-2-thione shown in the above scheme wherein $R^0$ is ethyl and $R_1$ is —$CH_2$-$C(O)SCH_3$ is reacted with benzyl α-(diethylphosphono)aminoacetate to form 2 of the formula

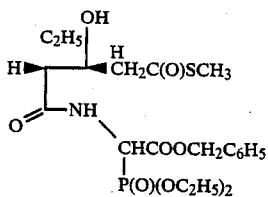

The chiral N-acyl thiazolidin-2-one precursors are prepared as described by Hsiao and Miller in copending application serial No. 780,101, filed September 25, 1985, and by Hsiao, C.-N., Ashburn, S. P., Miller, M. J., *Tetrahedron Letters*, 1985, 26, 4885, and Hsiao, C.-N., Liu, L., Miller, M. J., *J. Org. Chem.* 1987, 52, 2201.

The aminophosphono acetates 3 are exemplified by ethyl α-(dimethylphosphono)aminoacetate, t-butyl α-(dibenzylphosphono)aminoacetate, benzyl α-(diethylphosphono)aminoacetate, p-methoxybenzyl α-(diphenylphosphono)aminoacetate, diphenylmethyl α-(di-n-butylphosphono)aminoacetate, p-nitrobenzyl α-[di-(4chlorobenzyl)phosphono]aminoacetate and like amino acetates.

The β-hydroxy-α-phosphonomethyl amides 2 provided by this invention are useful for preparing the azetidinones 1. Examples of these β-hydroxy phosphonomethyl amides are shown below wherein the captioned terms have reference to formula 2 above.

Preferred β-hydroxy phosphonomethyl amides are represented by formula 2 wherein R is a protected amino group, $R_1$ is a group -(-$CH_2$-)$_n$Y and R is $C_1$-$C_4$ alkyl. A preferred amino-protecting group is the 4,5-diphenyl-4-oxazolin-2-one-1-yl group (abbreviated "Ox"). Further preferred amides are represented when Y is protected hydroxy or protected carboxy and n is 2, e.g., 2-benzyloxyethyl, 2-(4-methoxybenzyloxy)ethyl, 2-diphenylmethoxyethyl, 2-(trimethylsilyloxy)ethyl, 2-(t-butyldimethylsilyloxy)ethyl, 2-formylethyl, 2-ethoxycarbonylethyl, 2-benzyloxycarbonylethyl, 2-p-nitrobenzyloxycarbonylethyl, 2-diphenylmethyloxycarbonylethyl and 2-trimethylsilyloxycarbonylethyl.

Further preferred amides are represented by formula 2 wherein $R^0$ is $C_1$-$C_4$ alkyl and $R_1$ is a thio ester group -(-$CH_2$-)$_{1-2}$$C(O)SR_1'$ wherein $R_1'$ is 2-aminoethyl or 2-acetylaminoethyl.

The invention further provides the azetidinones represented by formula 1A below

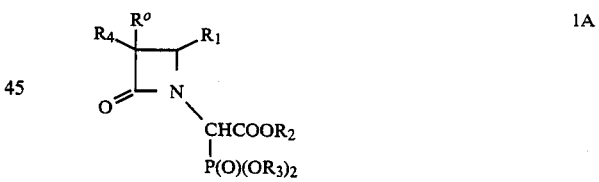

wherein $R_4$ is hydrogen, amino or protected amino;
$R^0$ is hydrogen when $R_4$ is amino or protected amino and is α-$C_1$-$C_4$ alkyl when $R_4$ is hydrogen;
$R_1$, $R_2$ and $R_3$ have the same meanings as defined for formula 1, and when $R_2$ is hydrogen, the base addition salts thereof, and when $R_4$ is amino, the acid addition salts thereof.

The 3β-aminoazetidinones represented by 1A wherein $R_4$ is amino are prepared by removing the protecting group from 1A wherein $R_4$ is protected amino.

Base addition salts of compound 1A when $R_2$ is hydrogen are the alkali metal and alkaline earth metal salts such as sodium, potassium, lithium and calcium, and the ammonium salts formed with ammonia and amines such as methylamine, diethylamine, triethylamine, aniline, benzylamine and like amines.

Acid addition salts of IA wherein $R_4$ is amino are the salts formed with mineral acids and sulfonic acids such as hydrochloric, hydrobromic, sulfuric, phsophoric, p-toluenesulfonic acid, methanesulfonic acid, naphthalenesulfonic acid and like acids. Such base and acid addition salts are obtained by conventional salt-forming procedures.

Preferred azetidinones 1A are represented when $R_4$ is amino or protected amino and $R_3$ is $C_1$-$C_4$ alkyl. A preferred protected amino group is the 4,5-diphenyl-4-oxazolin-2-one-1-yl group. Further preferred compounds are represented when $R_1$ is the group $-(CH_2)_n$-Y. A preferred Y group is carboxy. Further preferred azetidinones 1A are represented when $R^0$ is $C_1$-$C_4$ alkyl, especially ethyl, and $R_1$ is a thio ester group $-(CH_2)_{1-2}C(O)-S-R_1'$ wherein $R_1'$ is 2-aminoethyl or 2-acetylaminoethyl.

The azetidinones 1 are intermediates to fused bicyclic β-lactam antibacterials such as carbapenems and carbacephems. For example, the azetidinone 1 wherein $R^0$ is ethyl and $R_1$ is 2-benzyloxyethyl represented by the formula

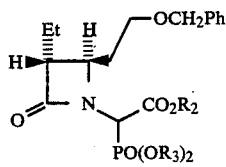

is debenzylated by hydrogenolysis over palladium on carbon catalyst to the corresponding 4β-(2-hydroxyethyl)azetidinone represented by the formula

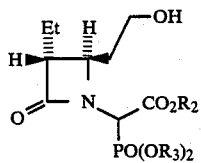

The alcohol is oxidized to the corresponding 4β2-formylmethyl compound, represented by the formula below, e.g., with pyridinium chlorochromate and neutral alumina.

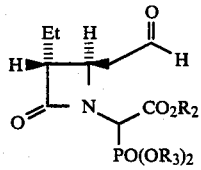

The aldehyde is treated with base, e.g., sodium hydride, in an inert anhydrous solvent such as THF to form decysteamino-PS-5 ester represented by the formula

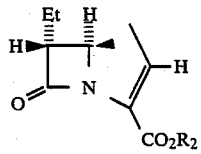

The above 4β-formylmethylazetidinone may also be converted to PS-5. The aldehyde is first converted by known procedures to the thio ester formed with a 2-(protected amino)ethylmercaptan and the latter on treatment with a base such as sodium hydride is cyclized to the carbapenem as shown below.

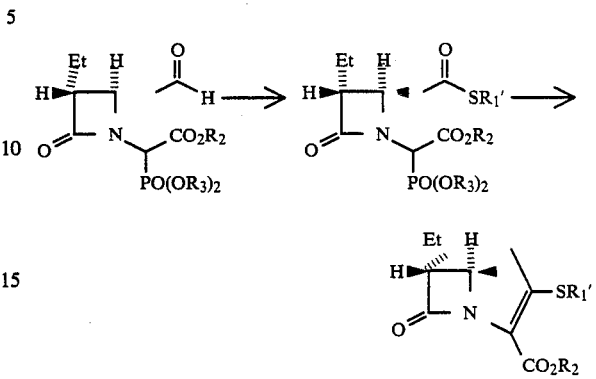

In a similar manner, 1-carbacephem compounds may be obtained with the azetidinone 1 wherein $R_1$ is a group represented by the formula $-CH_2CH_2-C(O)-SR_1$.

For example, a 3β-Ox-4β-(2-methylthiocarbonylethyl) substituted azetidinone 1 represented by the formula

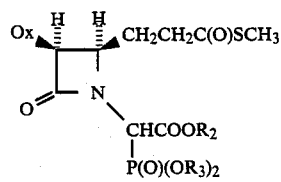

is treated with a base such as sodium hydride to form the 6β-(amino-protected)-3-methylthio-1-carba-3-cephem ester represented by the formula

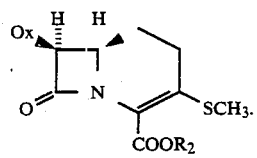

The azetidinones 1A wherein R is amino and $R_1$ is hydrogen or methyl are converted to antibacterial compounds represented by formula 4

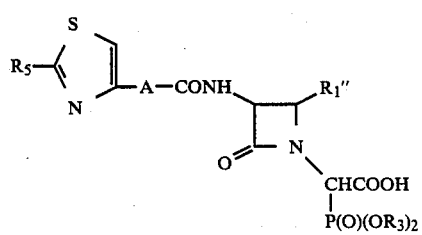

wherein $R_5$ is amino or protected amino;

A is $-CH_2-$, $-C(O)-$ or an oximino group represented by the formula

wherein $R_6$ is $C_1$-$C_6$ alkyl, $C_1$-$C_6$ alkyl substituted by halogen, cyano, amino; $C_1$-$C_4$ alkylamino, di-($C_1$-$C_4$ alkyl)amino, carboxy, $C_1$-$C_4$ alkoxycarbonyl or carbamoyl;

$R_1''$ is hydrogen or $C_1$-$C_4$ alkyl;

$R_3$ is $C_1$-$C_4$ alkyl, phenyl or benzyl or phenyl or benzyl mono-substituted by $C_1$-$C_4$ alkyl, $C_1$-$C_4$ alkoxy or halogen; and the pharmaceutically acceptable non-toxic salts thereof.

The term protected amino represented by $R_5$ refers to a conventional amino-protecting group as defined and exemplified for Formula 1 above. A preferred amino-protecting group $R_5$ is the triphenylmethyl(trityl) group. The 2-amino group of the thiazole ring is desirably protected during the preparation of 4 as described below.

The term $R_6$ refers to $C_1$-$C_6$ alkyl groups such as methyl, ethyl, n-propyl, isopropyl, n-butyl n-hexyl and like straight and branched chain alkyl groups; $C_1$-$C_6$ alkyl substituted by halogen refers to the alkyl group substituted by chloro, bromo or fluoro, e.g., 2-chloroethyl, 3-bromopropyl, 3-fluorobutyl, 3-fluoropropyl, 3-chloropropyl and the like; by cyano refers to such groups as cyanomethyl, 2-cyanoethyl, 2-cyanopropyl, 4-cyanobutyl and 2-cyanoprop-2-yl and the like; by amino refers to 2-aminoethyl, 3-aminopropyl, 2-aminopropyl, 5-aminopentyl, 3-aminohexyl and the like; by $C_1$-$C_4$ alkylamino refers to 2-methylaminoethyl, 2-ethylaminopropyl, 4-ethylaminobutyl, 3-isopropylaminobutyl and the like; by di-($C_1$-$C_4$ alkyl)amino refers to dimethylaminomethyl, 2-diethylaminoethyl, 3-dipropylaminopropyl, 4-dimethylaminobutyl, 6-diethylaminohexyl and the like; by carboxy refers to carboxymethyl, 2-carboxyethyl, 3-carboxypropyl, 2-carboxyprop-2-yl, 4-carboxybutyl and the like; and by $C_1$-$C_4$ alkoxycarbonyl refers to methoxycarbonylmethyl, 2-ethoxycarbonylethyl, 3-t-butyloxycarbonylpropyl, 2-t-butyloxycarbonylprop-2-yl, 3-isopropoxycarbonylpropyl, 4-ethoxycarbonylbutyl and the like.

The term $R_3$ has the same meanings as defined above for formulas 1 and 1A.

The compounds 4 are prepared by the N-acylation of azetidinone 1A, wherein $R_4$ is amino and $R_2$ is a carboxy-protecting group, with an active carboxy derivative of the acid

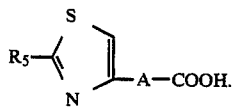

These acids which are obtained by known procedures include the 2-(2-aminothiazol-4-yl)acetic acid A=C-$H_2$—, the 2-(2-aminothiazol-4-yl)glyoxalic acid, A=—C(O)—, the 2-(2-aminothiazol-4-yl)-2-oximinoacetic acid, A=>C=N—$OR_6$, and the protected amino derivatives thereof. Active derivatives of these acids are preferably used in the N-acylation of 1A. Active esters such as those formed with N-hydroxybenzothiazole or N-hydroxysuccinimide can be used.

The N-acylation is carried out in an inert solvent by first forming the active ester and then adding the 3-aminoazetidinone 1A to the solution of the active ester. The active ester is prepared by mixing the acid with N-hydroxybenzothiazole in the presence of a dehydrating agent such as a carbodiimide, e.g., dicyclohexylcarbodiimide.

Following the N-acylation, the protected amino group $R_5$ and the protected carboxy group $R_2$ are deprotected to provide 4. The free acid 4 can be converted in a conventional manner with a base to a pharmaceutically acceptable salt. Such salts are, for example, the sodium, potassium or calcium salt or salts formed with amines such as, for example, benzylamine, dibenzylamine, ethanolamine, diethanolamine, procaine, triethylamine and β-phenethylamine.

The 3-aminoazetidinone (1A wherein $R_5$ is amino) is prepared by removing the protecting group from 1A wherein $R_5$ is protected amino. For example, a preferred protected amino group, the "Ox" group, is readily removed by hydrogenation over palladium on carbon catalyst in the presence of hydrochloric acid. For example, t-butyl α-(dimethylphosphono)-[3β-(4,5-diphenyl-4-oxazolin-2-one-3-yl)-4β-methylazetidin-2-one-1-yl]acetate is dissolved in ethanolic HCl and hydrogenated under 35 psi hydrogen pressure in the presence of 5% Pd-C to provide 1A wherein $R_4$ is amino, $R_1'$ is methyl, $R_2$ is t-butyl and $R_3$ is methyl.

Preferred compounds are represented when $R_5$ is amino, $R_1''$ is hydrogen or methyl, $R_3$ is $C_1$-$C_4$ alkyl and A is an oximino group. Further preferred compounds are represented when $R_6$ of the oximino group is $C_1$-$C_4$ alkyl or $C_1$-$C_4$ alkyl substituted by halogen, carboxy, $C_1$-$C_4$ alkoxycarbonyl or carbamoyl. Examples of such preferred compounds include the following:

α-(Dimethylphosphono)-[[3β-[2-(2-aminothiazol-4-yl)-2-methoxyiminoacetylamino]-4β-methylazetidin-2-one-1-yl]]acetic acid, α-Diethylphosphono-[[3β-[2-(2-aminothiazol-4-yl)-2-(2-carboxyprop-2-yl)oxyiminoacetylamino]azetidin-2-one-1-yl]]acetic acid, and α-(Diethylphosphono)-[[3β-2-(2-aminothiazol-4-yl)-2-(2-carboxyethyl)oxyiminoacetylamino]-4β-methylazetidin-2-one-1-yl]]acetic acid.

The oximino group can exist in syn and anti isomeric forms. The syn form of the oximino-substituted compounds is preferred.

A further preferred group of compounds 4 are represented when A is —$CH_2$—, $R_3$ is $C_1$-$C_4$ alkyl and $R_1''$ is hydrogen or methyl.

The compounds represented by formula 4 inhibit the growth of microorganisms pathogenic to man and animals and can be used to treat infections. For example, solutions of the compounds or, preferably, a pharmaceutically acceptable salt thereof can be made up into aqueous solutions for topical application to abrasions, cuts or lesions to prevent or treat infections. Antibacterial solutions at a concentration of between about 5% and about 50% w/v of antibiotic 4 are suitable for such use.

The following Examples are provided to further illustrate the invention in α-phosphonomethyl azetidinone acetates and are not intended to be limiting thereof.

EXAMPLE 1

2-(Trimethylsilyl)ethyl
α-dimethylphosphono-[3β-(4,5-diphenyl-4-oxazolin-
2-one-3-yl)-4α-methylazetidin-2-one-1-yl]acetate

A. Coupling to form phosphono amide

A mixture of Ox protected L-threonine (212 mg, 0.407 mmole), 2-(trimethylsilyl)ethyl α-(dimethylphosphono)glycinate (130 mg, 0.407 mmol) and hydroxybenzotriazole (69 mg, 0.509 mmol) in 3 ml of dry methylene chloride was cooled to 0° C. and a solution of dicyclohexylcarbodiimide (105 mg, 0.509 mmol) in methylene chloride was added dropwise over 30 minutes. The reaction mixture was allowed to warm to room temperature, and after 12 hours the reaction mixture was filtered to remove the insoluble dicyclohexylurea and the filtrate evaporated under vacuum to remove solvent. The residue was dissolved in 1 ml of benzene, the solution filtered and evaporated under vacuum. The residue was dissolved in ethyl acetate and the solution washed with 5% sodium bicarbonate solution, 0.5N citric acid solution and with brine, was dried with sodium sulfate and evaporated under vacuum. The crude product was purified by radial chromatography on silica gel (75% ethyl acetate-hexanes) to yield 110 mg, 52% of the phosphono amide of N-Ox protected L-threonine.

IR (neat): cm$^{-1}$ 3390, 3250, 2975, 1738, 1685, 1250, 1035, 865, 750 and 675.

NMR (CDCl$_3$): δ 0.03 (s, 9H), 0.05 (t, 2H), 1.07 (m, 2H), 1.28 (d, 2H), 3.81 (s, 3H), 3.86 (s, 3H), 4.31 (m, 2H), 4.50 (m, 1H), 5.12 (m, 1H), 5.23 (m, 1H), 7.22 (s, 5H), 7.55 (m, 5H), 7.92 (m, 1H), 8.09 (m, 1H).

B. Cyclization of phosphono amide

The phosphono amide (260 mg, 0.442 mmole) and triphenylphosphine (174 mg, 0.663 mmole, 1.5 eq.) were dissolved in 4 ml of dry THF and 4 ml of a solution of diisopropyl azodicarboxylate (134 mg, 0.663 mmol) was added dropwise via syringe with stirring. After stirring for 6 hours, the reaction mixture was evaporated under vacuum and the residue was chromatographed (radial) over silica gel with a gradient of 50% ethyl acetate/hexanes to 100% ethyl acetate to yield 61 mg of the title azetidinone (25% yield).

IR (CHCl$_3$): cm$^{-1}$ 2960, 1740, 1250, 1060 and 840.

NMR (200 MHz, CDCl$_3$): δ 0.03 (m, 9H), 1.20 (s, 3H), 1.22 (s, 3H), 1.45 (m, 2H), 3.82–3.95 (m, 8H), 4.25 (m, 2H), 4.92 (d, 1H), 5.12 (d, 1H), 7.22 (s, 5H), 7.43 (m, 5H), 7.57 (m, 5H).

EXAMPLE 2

Methyl
α-diethylphosphono-[3β-(4,5-diphenyl-4-oxazolin-
2-one-3-yl)azetidin-2-one-1-yl]acetate

A. Coupling to form phosphonomethyl amide

To a mixture of Ox protected serine dicyclohexylamine salt (247 mg, 0.488 mmol), methylamino(diethylphosphono)acetate (110 mg, 0.488 mmol) and N-hydroxybenzothiazole (82 mg, 0.610 mmol) in 5 ml of methylene chloride was added portionwise with stirring at room temperature 1-cyclohexyl-3-(morpholinoethyl)carbodiimide-metho-p-toluenesulfonate (258 mg, 0.610 mmol). After 12 hours the reaction mixture was diluted with 10 ml of methylene chloride and the mixture washed with 0.18M H$_2$SO$_4$, water and with brine and was dried over sodium sulfate. The dried mixture was evaporated under vacuum and the crude residue of product was purified by radial silica gel chromatography with 5% CH$_3$OH—CH$_2$Cl$_2$. There were obtained 130 mg (50% yield) of the hydroxyphosphonomethyl amide as a mixture of diastereomers.

IR (film): cm$^{-1}$ 3330, 2930, 2860, 1760, 1750, 1680, 1625, 1250, 1025 and 660.

NMR (200 MHz, CDCl$_3$): δ 8.00 (br d, 1H), 7.50 (m, 5H), 7.15 (s, 5H), 5.14 (d, 1H), 4.10–4.30 (m, 6H), 3.78 (s, 3H) 1.25 (m, 6H).

Mass Spectrum: 533 (M+1)

B. Cyclization

A solution of the hydroxy amide obtained above (50 mg, 0.094 mmol) and triphenylphosphine (30 mg, 0.115 mmol) in 1 ml of dry THF was cooled to about 0° C. and a solution of dimethyl azodicarboxylate (33 mg, 0.115 mmol) in 1 ml of THF was added slowly with stirring. After 30 minutes the mixture was evaporated under vacuum and the residue was chromatographed over silica gel (radial chromatography) with 50% ethyl acetate-hexanes. There were obtained 20 mg (42% yield) of the title azetidinone as a mixture of diastereomers.

IR (film): cm$^{-1}$ 2980, 2920, 1765, 1750, 1390, 1250, 1020, 740 and 590.

NMR (200 MHz): δ 7.40–7.70 (m, 5H), 7.15 (s, 9H), 5.10 (d, J=22 Hz, 1H), 4.98 (d, J=23 Hz, 1H), 5.00 (m, 1H), 4.80 (m, 1H), 4.10–4.40 (m, 6H), 3.80 (s, 3H), 3.78 (s, 3H), 1.30–1.55 (m, 6H)

Mass spectrum: 515 (M+1)

EXAMPLE 3

2-(Trimethylsilyl)ethyl
α-dimethylphosphono-[3α-ethyl-4β-(2-benzyloxyethyl)azetidin-2-one-1-yl]acetate

A. Coupling to form phosphono amide

To a solution of N-(2-ethyl-3-hydroxy-4-benzyloxyvaleryl)-4-methoxycarbonylthiazolidin-2-thione (277 mg, 0.676 mmol) and 2-(trimethylsilyl)ethyl α-dimethylphosphonoglycinate (216 mg, 0.676 mmol) in 2 ml of dry acetonitrile was added dimethylaminopyridine (20 mg). The reaction mixture was stirred for 24 hours at room temperature and was evaporated to a yellow oil. The crude oil was purified by flash chromatography over silica gel with 75% ethyl acetate-hexanes to yield 254 mg (70% yield) of the phosphonomethyl amide presented by the formula

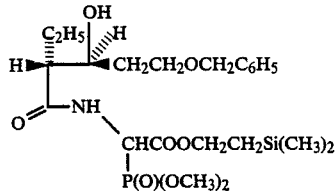

B. Cyclization to azetidinone

To a solution of the above amide (245 mg, 0.473 mmol) and riphenylphosphine (248 mg, 0.946 mmol, 2 eq.) in 5 ml of dry THF was added via syringe over 1 hour a solution of diisopropyl azodicarboxylate (191 mg, 0.946 mmol) in 5 ml of dry THF. After stirring for 12 hours at room temperature, the reaction mixture was evaporated under vacuum and the residue chromatographed (radial) over silica gel with 75% ethyl acetate-hexanes to provide the title azetidinone contaminated with triphenylphosphine oxide. The product was further purified by flash chromatography with 75% ethyl acetatehexanes. The product was further purified by trituration with diethyl ether.

NMR (200 MHz, CDCl$_3$): δ 0.04 (s, 9H), 0.99 (t, 2H), 1.24 (t, 3H), 1.70–2.00 (m, 2H), 2.30–2.60 (m, 2H), 2.95 (m, 1H), 3.55 (t, 2H), 3.82 (m, 6H), 4.25 (m, 4H), 4.48 (s, 2H), 5.03 (m, 1H), 7.31 (s, 5H). The title compound is represented by the formula

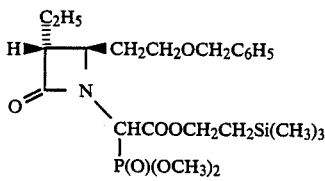

EXAMPLE 4

2-(Trimethylsilyl)ethyl α-dimethylphosphono-[3α-ethyl-4β-(2-hydroxyethyl)azetidin-2-one-1-yl]acetate The 4β-(2-benzyloxyethyl)azetidinone obtained as described by Example 3 was debenzylated to the title compound as follows.

A suspension of 10% Pd-C catalyst in 95% ethyl alcohol was prehydrogenated for 10 minutes and a solution of the azetidinone (Example 3, 125 mg) in 5 ml of ethyl alcohol was added to the suspension. The mixture was hydrogenated for 12 hours, filtered to remove catalyst, evaporated under vacuum and the residue flash chromatographed over silica gel with ethyl acetate to yield 48 mg (47% yield) of the title compound as a clear oil.

IR (film): cm$^{-1}$ 3440, 2955, 1755, 1735, 1250, 1040, 855 and 835.

NMR (200 MHz, CDCl$_3$): δ 0.06 (s, 9H), 1.04 (m, 5H), 1.60–2.10 (m, 3H), 2.30–2.50 (m, 1H), 2.92 (m, 1H), 3.55 (m, 1H), 3.88 (m, 8H), 4.29 (m, 2H), 5.10 (d, J=24 Hz, 1H).

EXAMPLE 5

2-(Trimethylsilyl)ethyl α-dimethylphosphono-[3α-ethyl-4β-(formylmethyl)azetidin-2-one-1-yl]acetate A mixture of pyridinium chlorochromate (28 mg, 0.128 mmol) and neutral alumina (140 mg) was stirred in 2 ml of dry methylene chloride for 10 minutes. To the orange suspension was added dropwise at 10° C. a solution of the 4-(2-hydroxyethyl)azetidinone obtained as described by Example 4 (35 mg, 0.085 mmol) in 2 ml of dry methylene chloride. The reaction mixture turned dark brown as the reaction progressed. After stirring for 5 hours at room temperature, 5 ml of diethyl ether were added and the mixture filtered through a filter aid. The filter aid was washed with ethyl acetate and the filtrate was evaporated under vacuum to yield 24 mg (63% yield) of the title aldehyde as an oil.

NMR (200 MHz, CDCl$_3$): δ 0.01 (s, 9H), 1.06 (m, 3H), 1.60–2.00 (m, 6H), 2.95 (m, 1H), 3.85 (m, 7H), 4.30 (m, 2H), 5.10 (d, J=24 Hz, 1H), 9.82 (d, 1H).

EXAMPLE 6

2-(Trimethylsilyl)ethyl 6α-ethyl-1-carba(dethia)-2-penem-3-carboxylate

This example illustrates the conversion of an azetidinone, obtained in the process of the invention, to a penem.

A 6% dispersion of sodium hydride (1.5 mg, 0.063 mmol) was washed with hexanes and cooled to −20° C. A solution of the azetidinone aldehyde prepared as described by Example 5 (10 mg) in 1 ml of THF was added to the washed sodium hydride. The reaction mixture was allowed to warm to room temperature over 30 minutes. After 6 hours the reaction mixture was filtered through silica gel with 25% ethyl acetatehexanes. The filtrate was evaporated under vacuum and the product penem further purified by flash chromatography with 25% ethyl acetate-hexanes. There were obtained 2 mg of the title penem.

IR: cm$^{-1}$ 2960, 2930, 2860, 1770–1780, 1730, 1250, 860 and 835.

NMR (200 MHz, CDCl$_3$): δ 0.90–1.10 (m, 2H), 1.08 (dt, 3H) 1.85 (m, 2H), 2.83 (m, 2H), 3.13 (m, 1H), 4.00 (m, 1H), 4.33 (m, 2H), 6.42 (m, 1H).

EXAMPLE 7 p-Nitrobenzyl α-(dimethylphosphono)-α-[3α-ethyl-4β-[2-[dimethyl-(2,3-dimethylbutan-2-yl)silyloxy]ethyl]-azetidin-2-one-1-yl]acetate A solution of N-[2-ethyl-3-hydroxy-4-[dimethyl(2,3-dimethylbutan-2-yl)silyloxy]valeryl]-4-methoxycarbonylthiazolidin-2-thione (450 mg, 0.97 mmol), HBT (164 mg, 1.2 mmol) and pyridine (76 mg, 0.97 mmol) in dry acetonitrile (0.5 ml) was stirred for 1 hour at room temperature and p-nitrobenzyl α-(dimethylphosphono)aminoacetate (387 mg, 1.21 mmol) in acetonitrile (0.5 ml) containing a few crystals of DMAP was added. As the reaction proceeded, the yellow color disappeared and a precipitate developed. After 48 hours the reaction mixture was diluted with ethyl acetate and washed with 5% sodium bicarbonate and brine, was dried over sodium sulfate and evaporated under vacuum. The crude oil was purified by chromatography over silica gel with 50% ethyl acetate/hexanes to 100% ethyl acetate to yield 144 mg (22% yield) of the β-hydroxy α-phosphonoamide as a light yellow oil. The ratio of diastereoisomers was about 1:1.

IR cm$^{-1}$: 3410, 3270, 2955, 2870, 1750, 1670 (broad), 1520, 1345, 1250, 1030 (broad), 830.

NMR (200 MHz, CDCl$_3$): δ 0.09 (s, 6H), 0.82 (s, 6H), 0.89 (d, J=7.5 Hz, 6H), 1.05 (m, 3H), 1.50–1.90 (m, 5H), 2.30 (m, 1H), 3.74 (d, 3H), 3.80 (d, H), 3.70 (m, 1H), 3.98 (m, 2H), 5.15–5.50 (m, 3H), 7.06 (m, 1H), 7.54 (d, J=8.6 Hz, 2H), 8.19 (d, J=8.6 Hz, 2H).

The β-hydroxy α-phosphonoamide is cyclized in the process of this invention to provide the title compound.

I claim:

1. A compound of the formula

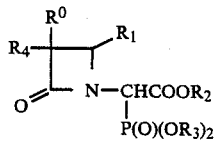

wherein
R₄ is hydrogen, amino or protected amino;
R⁰ is hydrogen when R₄ is protected amino or amino, or C₁-C₄ alkyl when R₄ is hydrogen;
R₁ is hydrogen, methyl, a group —(CH₂)ₙY wherein Y is hydroxy, protected hydroxy, hydroxymethyl, protected hydroxymethyl, halogen, carboxy or protected carboxy; n is 1 or 2; or R₁ is a thioester group —(CH₂)₁₋₂C(O—SR₁' wherein R₁' is C₁-C₄ alkyl or C₁-C₄ alkyl substituted by amino, acetylamino, C₁-C₄ alkylamino or di-(C₁-C₄ alkyl)amino;
R₂ is hydrogen or a carboxy-protecting group;
R₃ is C₁-C₄ alkyl, phenyl or benzyl, or phenyl or benzyl mono-substituted by C₁-C₄ alkyl, halogen or C₁-C₄ alkoxy; and when R₂ is hydrogen, the base addition salts thereof, and when R₄ is amino, the acid addition salts thereof.

2. The compound of claim 1 wherein R is protected amino or amino or an acid addition salt.

3. The compound of claim 2 wherein R₄ is protected amino and R₁ is hydrogen or methyl.

4. The compound of claim 1 wherein R₄ is hydrogen and R⁰ is C₁-C₄ alkyl.

5. The compound of claim 4 wherein R⁰ is ethyl and R₁ is —(CH₂)ₙY.

6. The compound of claim 5 wherein R₁ is 2-benzyloxyethyl, 2-hydroxyethyl, or 2-carboxyethyl.

7. The compound of claim 6 of the formula

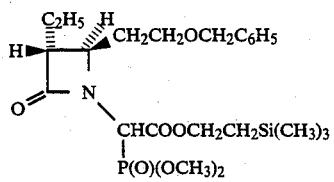

8. The compound of claim 6 of the formula

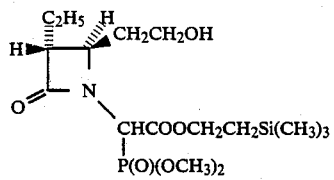

9. The compound of the formula

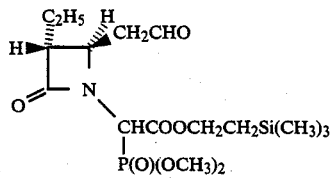

10. The compound of claim 4 wherein R₁ is a thioester group of the formula —(CH₂)₁₋₂C(O)SR₁''.

11. The compound of claim 3 wherein R₄ is

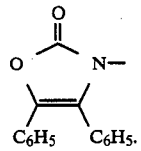

12. The compound of claim 11 of the formula

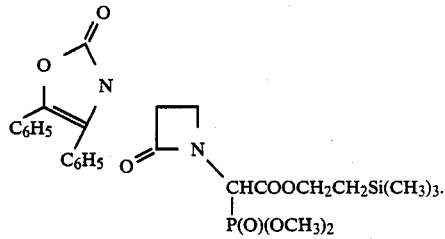

13. The compound of claim 11 of the formula

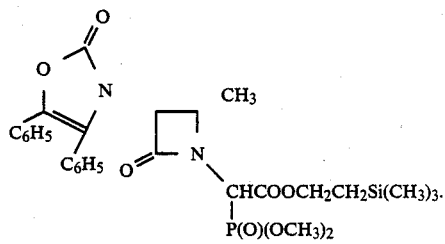

14. The compound of the formula

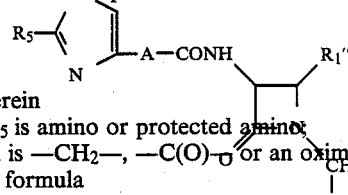

wherein
R₅ is amino or protected amino;
A is —CH₂—, —C(O)— or an oximino group of the formula

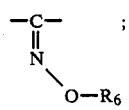

wherein
R₆ is C₁-C₆ alkyl; C₁-C₆ alkyl substituted by halogen, cyano, amino, C₁-C₄ alkylamino, di-(C₁-C₄ alkyl)amino, carboxy, C₁-C₄ 1 alkoxycarbonyl or carbamoyl;
R₁'' is hydrogen or C₁-C₄ alkyl;
R₃ is C₁-C₄ alkyl, phenyl or benzyl, or phenyl or benzyl mono-substituted by C₁-C₄ alkyl, C₁-C₄ alkoxy or halogen; and the pharmaceutically acceptable non-toxic salts thereof.

15. The compound of claim 14 wherein R₅ is amino, A is an oximino group >C=N—OR₆ in the syn form.

16. The compound of claim 15 wherein R₆ is C₁-C₄ alkyl or C₁14 C₄ alkyl substituted by halogen, carboxy, C₁-C₄ alkoxycarbonyl or carbamoyl.

17. The compound of claim 16 wherein R₆ is methyl, carboxymethyl, 2-carboxyethyl, 2-carboxyprop-2-yl or 2-ethoxycarbonylethyl.

* * * * *

UNITED STATES PATENT AND TRADEMARK OFFICE
CERTIFICATE OF CORRECTION

PATENT NO. : 4,820,815

DATED : April 11, 1989

INVENTOR(S) : Marvin J. Miller

It is certified that error appears in the above-identified patent and that said Letters Patent is hereby corrected as shown below:

Column 2, line 1, "$C_{1}$-$C_{4}$ alkyl," should read -- $C_1$-$C_4$ alkyl, --.

Column 2, line 38, "$C_1 \equiv C_3$" should read -- $C_1$-$C_3$ --.

Column 5, lines 42 thru 50,

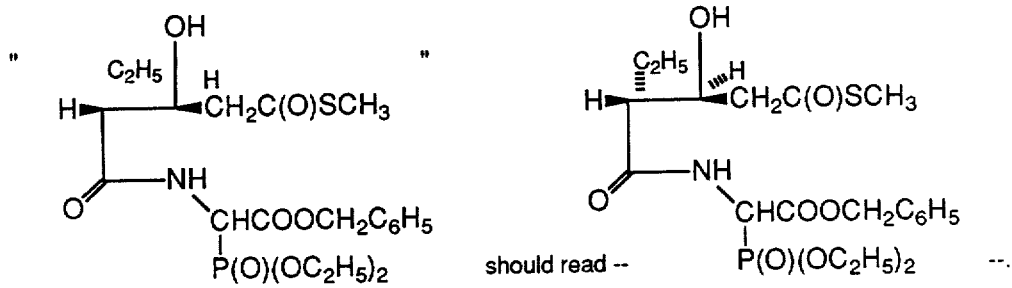

Column 5, line 64, "(4chlorobenzyl)" should read -- (4-chlorobenzyl) --.

Column 7, line 41, "462" should read -- 4β --.

UNITED STATES PATENT AND TRADEMARK OFFICE
CERTIFICATE OF CORRECTION

PATENT NO. : 4,820,815

DATED : April 11, 1989

INVENTOR(S) : Marvin J. Miller

It is certified that error appears in the above-identified patent and that said Letters Patent is hereby corrected as shown below:

Column 12, line 64, "riphenylphosphine" should read -- triphenylphosphine --.

Column 13, line 6, "acetatehexanes." should read -- acetate-hexanes. --.

Column 14, line 15, "acetatehex-" should read -- acetate-hex- --.

Column 15, line 10, "C(O) —— SR$_1$" should read -- C(O) —— SR$_1$' --.

Column 15, line 65, "C(O)SR$_1$." should read -- C(O)SR$_1$'. --.

Column 16, lines 10 thru 20

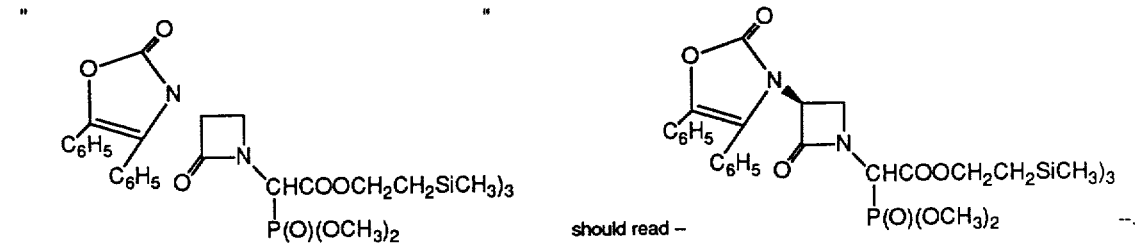

should read --

Column 16, lines 21 thru 31

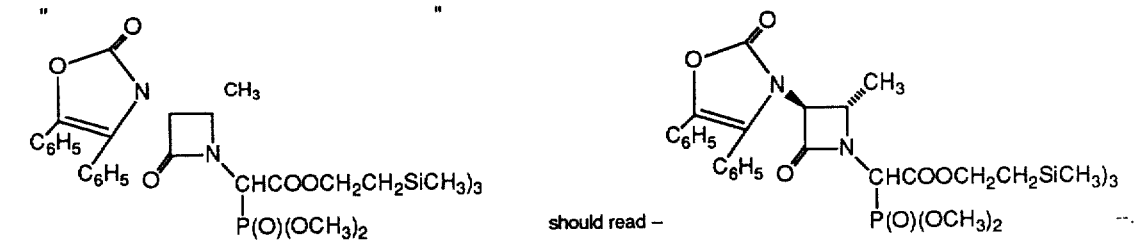

should read --

UNITED STATES PATENT AND TRADEMARK OFFICE
CERTIFICATE OF CORRECTION

PATENT NO. : 4,820,815

DATED : April 11, 1989

INVENTOR(S) : Marvin J. Miller

It is certified that error appears in the above-identified patent and that said Letters Patent is hereby corrected as shown below:

Column 16, lines 34 thru 46

"

14. The compound of the formula

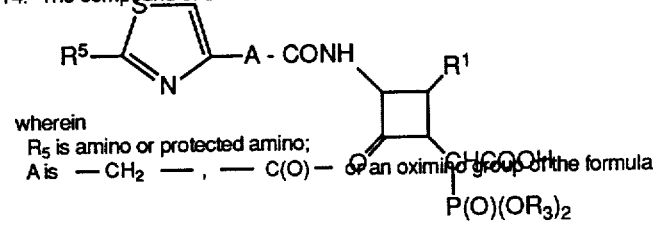

wherein
$R_5$ is amino or protected amino;
A is — $CH_2$ —, — C(O) — or an oximino group of the formula

"

should read —

14. The compound of the formula

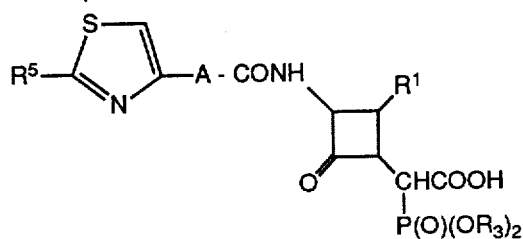

wherein
$R_5$ is amino or protected amino;
A is — $CH_2$ —, — C(O) — or an oximino group of the formula —.

UNITED STATES PATENT AND TRADEMARK OFFICE
CERTIFICATE OF CORRECTION

PATENT NO. : 4,820,815

DATED : April 11, 1989

INVENTOR(S) : Marvin J. Miller

It is certified that error appears in the above-identified patent and that said Letters Patent is hereby corrected as shown below:

Column 16, line 61, "$C_1 14 C_4$" should read --$C_1-C_4$--.

Signed and Sealed this

Fifth Day of February, 1991

*Attest:*

HARRY F. MANBECK, JR.

*Attesting Officer*  *Commissioner of Patents and Trademarks*